US00PP31925P2

(12) United States Plant Patent
Laughner

(10) Patent No.: US PP31,925 P2
(45) Date of Patent: Jun. 30, 2020

(54) ***OSTEOSPERMUM* PLANT NAMED 'BALSERCORIC'**

(50) Latin Name: *Osteospermum ecklonis*
Varietal Denomination: Balsercoric

(71) Applicant: Ball Horticultural Company, West Chicago, IL (US)

(72) Inventor: Linda Laughner, Ventura, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/602,014

(22) Filed: Jul. 19, 2019

(51) Int. Cl.
*A01H 5/02* (2018.01)
*A01H 6/14* (2018.01)

(52) U.S. Cl.
USPC ..... Plt./360

(58) Field of Classification Search
USPC ..... Plt./263.1, 360
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Osteospermum* plant named 'Balsercoric', characterized by its medium coral-red and light purple colored inflorescences, dark green-colored foliage, and moderately vigorous, upright-mounded growth habit, is disclosed.

1 Drawing Sheet

Latin name of genus and species of plant claimed: *Osteospermum ecklonis.*

Variety denomination: 'Balsercoric'.

BACKGROUND OF THE INVENTION

The present invention relates to a new and distinct cultivar of *Osteospermum* plant botanically known as *Osteospermum ecklonis* and hereinafter referred to by the cultivar name 'Balsercoric'.

The new cultivar originated in a controlled breeding program in Santa Paula, Calif. during summer 2014. The objective of the breeding program was the development of *Osteospermum* cultivars that are freely flowering with unique flower coloration and a freely branching, upright-mounded growth habit.

The new *Osteospermum* cultivar is the result of open-pollination. The female (seed) parent of the new cultivar is the proprietary *Osteospermum ecklonis* breeding selection coded 58952-2, not patented, characterized by its coral-orange colored inflorescences having a large purple-colored center, medium green-colored foliage, and moderately vigorous, upright-mounded growth habit. The male (pollen) parent of the new cultivar is unknown. The new cultivar was discovered and selected as a single flowering plant within the progeny of the above stated open-pollination during February 2015 in a controlled environment in Santa Paula, Calif.

Asexual reproduction of the new cultivar by terminal stem cuttings since February 2015 in Santa Paula, Calif. and Arroyo Grande Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsercoric' as a new and distinct cultivar of *Osteospermum* plant:

1. Medium coral-red and light purple colored inflorescences;
2. Dark green-colored foliage; and
3. Moderately vigorous, upright-mounded growth habit.

Plants of the new cultivar differ from plants of the female parent primarily in having inflorescences with a larger diameter, a redder shade of coral, and a smaller and lighter purple-colored center.

Of the many commercially available *Osteospermum* cultivars, the most similar in comparison to the new cultivar is Blue Eyed Beauty 'Balostlueye', U.S. Plant Pat. No. 26,150. However, in side-by-side comparison, plants of the new cultivar differ from plants of 'Balostlueye' in at least the following characteristics:

1. Plants of the new cultivar have a ray floret color that is more red with a lighter purple-colored center than plants of 'Balostlueye'; and
2. Plants of the new cultivar have more branches per plant than plants of 'Balostlueye'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balsercoric'. The plants were grown in 4.5-inch pots for 14 weeks in a greenhouse in West Chicago, Ill.

DETAILED BOTANICAL DESCRIPTION

Figure 1:
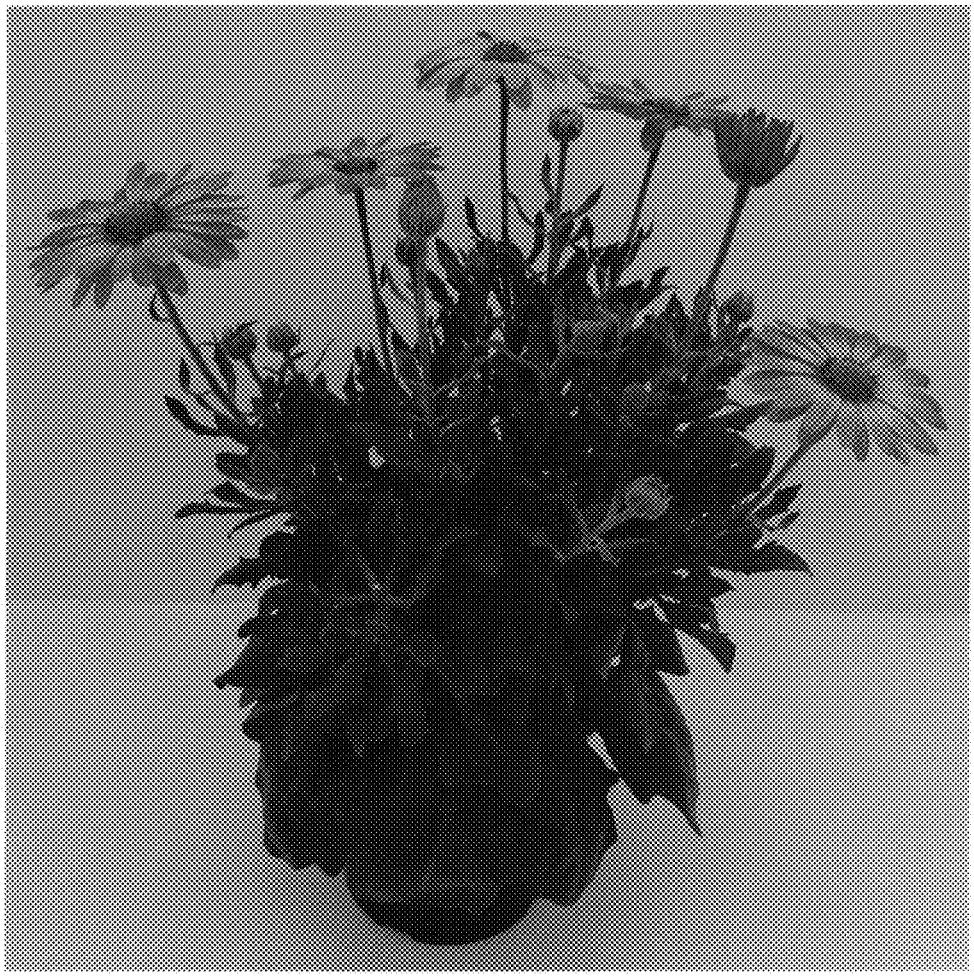
FIG. 1 illustrates a side view of the overall growth and flowering habit of 'Balsercoric'.
Figure 2:
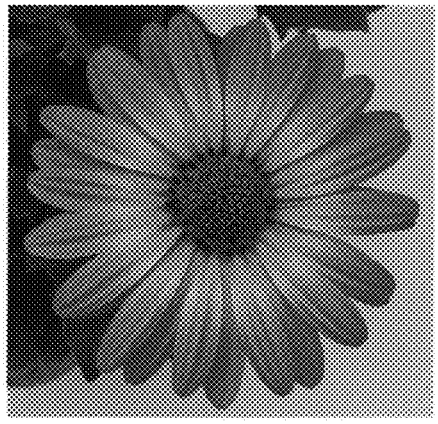
FIG. 2 illustrates a close-up view of an individual inflorescence of 'Balsercoric'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in May 2019 under natural light conditions in West Chicago, Ill.

The following descriptions and measurements describe approximately 6-month old plants produced from cuttings from stock plants and grown in a glass-covered greenhouse under conditions comparable to those used in commercial practice. The plants were grown in West Chicago, Ill. in 4.5-inch pots for approximately 14 weeks utilizing a soilless growth medium. Greenhouse temperatures were maintained at approximately 67° F. to 72° F. (19° C. to 22° C.) during the day and approximately 65° F. to 68° F. (18° C. to 20° C.) during the night. Supplemental lighting was used. Measurements and numerical values represent averages of typical plants.

Botanical classification: *Osteospermum ecklonis* 'Balsercoric'.

Parentage:

*Female parent*.—Proprietary *Osteospermum ecklonis* breeding selection coded 58952-2, not patented.

*Male parent*.—Unknown.

Propagation:

*Type cutting*.—Terminal stem.

*Time to initiate roots*.—Approximately 9 to 12 days.

*Time to produce a rooted cutting*.—Approximately 21 to 28 days.

*Root description*.—Fibrous.

*Rooting habit*.—Freely branching.

Plant description:

*Commercial crop time*.—Approximately 10 to 13 weeks from a rooted cutting to finish in a 10 cm pot.

*Growth habit and general appearance*.—Moderately vigorous, upright-mounded.

*Size*.—Height from soil level to top of plant plane: Approximately 23.0 cm. Width: Approximately 26.0 cm.

*Branching habit*.—Freely branching, pinching enhances basal branching. Quantity of main branches per plant: Approximately 8.

*Branch*.—Strength: Strong. Length to base of peduncle: Approximately 12.0 cm. Diameter: Approximately 4.0 mm. Length of central internode: Approximately 5.0 mm. Texture: Glabrous. Color of young and mature stems: 145A.

Foliage description:

*General description*.—Quantity of leaves per main branch: Approximately 18. Fragrance: Moderate. Form: Simple. Arrangement: Alternate.

*Leaves*.—Aspect: Acute angle to stem becoming an obtuse angle with age. Shape: Spatulate. Margin: Widely dentate. Apex: Acute. Base: Attenuate. Venation pattern: Pinnate. Length of mature leaf: Approximately 5.0 cm. Width of mature leaf: Approximately 2.8 cm. Texture of upper and lower surfaces: Sparsely pubescent, densely pubescent on margins. Color of upper surface of young and mature foliage: NN137A with venation of 146C to indistinguishable. Color of lower surface of young and mature foliage: 137B with venation of 146C to indistinguishable.

*Petiole*.—Length: Approximately 2.0 cm. Diameter: Approximately 4.0 mm. Texture: Densely pubescent on flattened edges. Color: 146C.

Flowering description:

*Flowering habit*.—'Balsercoric' is freely flowering under outdoor growing conditions with substantially continuous blooming from spring through autumn and year-round in greenhouse environment.

*Lastingness of individual inflorescence on the plant*.—Approximately 8 to 10 days.

Inflorescence description:

*General description*.—Type: Solitary, composite. Persistent. Shape: Round. Aspect: Facing upward. Arrangement: Terminal, held above the foliage, arising from leaf axils. Disc and ray florets develop acropetally on a capitulum. Fragrance: Faint. Quantity per plant: Approximately 5. Diameter: Approximately 6.7 cm. Depth: Approximately 1.8 cm.

*Peduncle*.—Strength: Strong. Aspect: Erect. Length: Approximately 6.5 cm. Diameter: Approximately 2.5 mm. Texture: Glandular pubescent. Gland color: Colorless. Color: 144A.

*Bud*.—Rate of opening: Generally takes 4 to 6 days for bud to progress from first color to fully open flower. Quantity per plant: Approximately 9.

*Bud just before opening*.—Shape: Ovoid. Length: Approximately 1.4 cm. Diameter: Approximately 1.2 cm. Color: 154B.

*Ray florets*.—Quantity per inflorescence: Approximately 28. Arrangement: Imbricate in a single whorl. Aspect: Initially at acute angle to disc, becoming perpendicular at maturity and downward turning as senesce. Shape: Oblanceolate. Margin: Entire. Apex: Emarginate with three tips. Base: Attenuate. Length: Approximately 3.0 cm. Width: Approximately 8.0 mm. Texture of upper surface: Glabrous, ribbed longitudinally. Texture of lower surface: Glabrous with a densely pubescent base, ribbed longitudinally. Color of upper surface when first open: 179C at apex transitioning at center to 4D with a faint overlay of 179C, base of 77B to 77C. Color of lower surface when first and fully open: 168D. Color of upper surface when fully open: 179B to 179C at apex transitioning at center to 4D, base of 77C.

*Disc florets*.—Quantity per inflorescence: Approximately 115. Arrangement: Massed in center of inflorescence. Shape: Tubular. Margin: Entire. Apex: Five to six acute tips. Base: Fused. Length: Approximately 9.0 mm. Diameter at apex: Approximately 2.0 mm. Diameter at base: Approximately 1.0 mm. Texture: Glabrous with a sparsely pubescent outer surface. Color when fully open: Closest to N155D with a faint overlay and tips of 185C, base of 155C.

*Disc*.—Diameter: Approximately 1.4 cm. Depth: Approximately 6.0 mm.

*Receptacle*.—Shape: Conical. Height: Approximately 2.0 mm. Diameter: Approximately 6.0 mm. Color: 145D.

*Phyllaries*.—Quantity per inflorescence Approximately 28. Arrangement: Imbricate, in a single whorl. Shape: Linear to lanceolate. Margin: Entire. Apex: Acute. Base: Truncate. Length: Approximately 1.2 cm. Width: Approximately 1.0 mm to 2.0 mm. Texture of upper or inner surface: Glabrous. Texture of lower or outer surface: Mixture of glandular and non- glandular pubescence. Gland color: Colorless, transparent. Color of upper or inner surface: 138B. Color of lower or outer surface: 138A.

*Reproductive organs*.—Androecium: Present on disc florets only. Stamen quantity: 5 per floret, fused around the style. Stamen length: Approximately 5.0 mm. Anther shape: Linear. Anther length: Approximately 2.0 mm. Anther color: 187A to N186A. Pollen amount: Abundant. Pollen color: 23A. Gynoecium: Present on ray and disc florets. Pistil quantity: 1 per floret. Pistil length: Approximately 9.0 mm. Stigma shape: Two thick lobes positioned closely together, appearing rounded. Stigma length: Less than 1 mm. Stigma color: 187A. Style length: Approximately 6.0 mm. Style color: NN155D. Ovary length: Approximately 3.0 mm. Ovary color: 155C.

Seed and fruit production: Neither seed nor fruit production has been observed.

Disease and pest resistance: Resistance to pathogens and pests common to *Osteospermum* has not been observed.

What is claimed is:

1. A new and distinct cultivar of *Osteospermum* plant named 'Balsercoric', substantially as herein illustrated and described.

* * * * *